US012773454B2

(12) United States Patent
Brzeczko et al.

(10) Patent No.: US 12,773,454 B2
(45) **Date of Patent: *Oct. 27, 2026**

(54) METHODS AND COMPOSITIONS FOR SELF-REGULATED RELEASE OF ACTIVE PHARMACEUTICAL INGREDIENT

(71) Applicant: Acura Pharmaceuticals, Inc., Palatine, IL (US)

(72) Inventors: Albert W. Brzeczko, Roswell, GA (US); R. Gary Hollenbeck, Ellicott City, MD (US)

(73) Assignee: Acura Pharmaceuticals, Inc., Palatine, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/539,830

(22) Filed: Dec. 14, 2023

(65) Prior Publication Data

US 2024/0108726 A1 Apr. 4, 2024

Related U.S. Application Data

(60) Continuation of application No. 17/366,256, filed on Jul. 2, 2021, now Pat. No. 11,857,629, which is a continuation of application No. 16/899,529, filed on Jun. 11, 2020, now Pat. No. 11,083,794, which is a continuation of application No. 16/041,331, filed on Jul. 20, 2018, now Pat. No. 10,688,184, which is a division of application No. 15/588,982, filed on May 8, 2017, now Pat. No. 10,441,657, which is a continuation of application No. 15/074,458, filed on Mar. 18, 2016, now Pat. No. 9,662,393, which is a continuation of application No. 14/790,113, filed on Jul. 2, 2015, now Pat. No. 9,320,796, which is a continuation of application No. 14/091,817, filed on Nov. 27, 2013, now Pat. No. 9,101,636.

(60) Provisional application No. 61/731,901, filed on Nov. 30, 2012.

(51) Int. Cl.

| | |
|---|---|
| ***A61K 47/02*** | (2006.01) |
| ***A61K 9/20*** | (2006.01) |
| ***A61K 31/5517*** | (2006.01) |
| ***A61K 47/32*** | (2006.01) |

(52) U.S. Cl.

CPC ............ *A61K 47/02* (2013.01); *A61K 9/2009* (2013.01); *A61K 9/2027* (2013.01); *A61K 9/2077* (2013.01); *A61K 31/5517* (2013.01); *A61K 47/32* (2013.01)

(58) Field of Classification Search

None

See application file for complete search history.

(56) References Cited

U.S. PATENT DOCUMENTS

| | | | |
|---|---|---|---|
| 3,065,143 | A | 11/1962 | Christenson et al. |
| 3,260,646 | A | 7/1966 | Paulsen et al. |
| 4,070,494 | A | 1/1978 | Hoffmeister et al. |
| 4,175,119 | A | 11/1979 | Porter |
| 4,221,778 | A | 9/1980 | Raghunathan |
| 4,389,393 | A | 6/1983 | Schor et al. |
| 4,457,933 | A | 7/1984 | Gordon et al. |
| 4,459,278 | A | 7/1984 | Porter |
| 4,599,342 | A | 7/1986 | LaHann |
| 4,610,870 | A | 9/1986 | Jain et al. |
| 4,666,705 | A | 5/1987 | DeCrosta et al. |
| 4,800,083 | A | 1/1989 | Hom et al. |
| 4,801,461 | A | 1/1989 | Hamel |
| 4,915,952 | A | 4/1990 | Ayer et al. |
| 4,952,402 | A | 8/1990 | Sparks |
| 5,059,600 | A | 10/1991 | Gawin et al. |
| 5,073,380 | A | 12/1991 | Babu |
| 5,075,114 | A | 12/1991 | Roche |
| 5,084,278 | A | 1/1992 | Mehta |
| 5,098,715 | A | 3/1992 | McCabe |
| 5,114,942 | A | 5/1992 | Gawin et al. |
| 5,273,758 | A | 12/1993 | Royce |
| 5,284,662 | A | 2/1994 | Koparkar et al. |
| 5,330,766 | A | 7/1994 | Morella et al. |
| 5,405,617 | A | 4/1995 | Gowan |
| 5,431,916 | A | 7/1995 | White |
| 5,484,606 | A | 1/1996 | Dhabhar |
| 5,508,042 | A | 4/1996 | Oshlack et al. |
| 5,558,879 | A | 9/1996 | Chen |
| 5,654,005 | A | 8/1997 | Chen |
| 5,741,524 | A | 4/1998 | Staniforth et al. |
| 5,807,579 | A | 9/1998 | Vilkov |
| 5,840,337 | A | 11/1998 | Cody |
| 5,858,409 | A | 1/1999 | Karetny |
| 5,895,663 | A | 4/1999 | Irwin et al. |
| 5,916,590 | A | 6/1999 | Cody et al. |
| 5,919,481 | A | 7/1999 | Cody et al. |
| 5,955,107 | A | 9/1999 | Augello |
| 5,968,551 | A | 10/1999 | Oshlack et al. |
| 5,997,905 | A | 12/1999 | McTeigue |
| 6,024,980 | A | 2/2000 | Hoy |

(Continued)

OTHER PUBLICATIONS

Examination Report dated Jan. 9, 2024, of counterpart Australian Patent Application No. 2023200124.

*Primary Examiner* — Melissa S Mercier

(74) *Attorney, Agent, or Firm* — Offit Kurman; Christopher I. Halliday; Chad Sayala

(57) ABSTRACT

An abuse deterrent pharmaceutical composition including a pharmaceutically active ingredient; an acid soluble ingredient; and a buffering ingredient; wherein the acid soluble ingredient and the buffering ingredient retard release of the active pharmaceutical ingredient when the composition is ingested in excess of an intended dosage.

6 Claims, 5 Drawing Sheets

(56) References Cited

U.S. PATENT DOCUMENTS

| | | | |
|---|---|---|---|
| 6,027,746 | A | 2/2000 | Lech |
| 6,136,864 | A | 10/2000 | Nichols et al. |
| 6,153,621 | A | 11/2000 | Hamann |
| 6,197,314 | B1 | 3/2001 | Elnig |
| 6,210,710 | B1 | 4/2001 | Skinner |
| 6,217,903 | B1 | 4/2001 | Skinner |
| 6,228,863 | B1 | 5/2001 | Palermo et al. |
| 6,248,363 | B1 | 6/2001 | Patel et al. |
| 6,277,409 | B1 | 8/2001 | Luber |
| 6,294,192 | B1 | 9/2001 | Patel |
| 6,309,663 | B1 | 10/2001 | Patel et al. |
| 6,309,668 | B1 | 10/2001 | Bastin et al. |
| 6,340,471 | B1 | 1/2002 | Kershman et al. |
| 6,352,721 | B1 | 3/2002 | Faour |
| 6,358,525 | B1 | 3/2002 | Guo |
| 6,359,011 | B1 | 3/2002 | Bess et al. |
| 6,375,957 | B1 | 4/2002 | Kaiko et al. |
| 6,383,471 | B1 | 5/2002 | Chen et al. |
| 6,432,442 | B1 | 8/2002 | Buehler |
| 6,471,991 | B2 | 10/2002 | Robinson |
| 6,488,963 | B1 | 12/2002 | McGinley et al. |
| 6,491,949 | B2 | 12/2002 | Faour et al. |
| 6,495,529 | B1 | 12/2002 | Booth |
| 6,500,459 | B1 | 12/2002 | Chhabra |
| 6,514,531 | B1 | 2/2003 | Alaux et al. |
| 6,524,618 | B1 | 2/2003 | Kumar et al. |
| 6,541,025 | B1 | 4/2003 | Kershman et al. |
| 6,551,617 | B1 | 4/2003 | Corbo |
| 6,559,159 | B2 | 5/2003 | Carroll et al. |
| 6,572,885 | B2 | 6/2003 | Oashlack et al. |
| 6,589,556 | B2 | 7/2003 | Cheruki et al. |
| 6,592,901 | B2 | 7/2003 | Durig et al. |
| 6,593,367 | B1 | 7/2003 | Dewey et al. |
| 6,607,748 | B1 | 8/2003 | Lenaerts |
| 6,613,357 | B2 | 9/2003 | Faour |
| 6,753,009 | B2 | 6/2004 | Luber et al. |
| 6,800,668 | B1 | 10/2004 | Odidi |
| 6,814,979 | B2 | 11/2004 | Rudnic |
| 6,923,988 | B2 | 8/2005 | Patel et al. |
| RE39,069 | E | 4/2006 | Faous |
| 7,090,867 | B2 | 8/2006 | Odidi et al. |
| 7,101,572 | B2 | 9/2006 | Santos |
| 7,141,250 | B2 | 11/2006 | Oshlack et al. |
| 7,144,587 | B2 | 12/2006 | Oshlack et al. |
| 7,157,100 | B2 | 1/2007 | Doshi et al. |
| 7,157,103 | B2 | 1/2007 | Sackler |
| 7,192,966 | B2 | 3/2007 | May-Alvarez |
| 7,201,920 | B2 | 4/2007 | Kumar et al. |
| 7,332,182 | B2 | 2/2008 | Sackler |
| 7,374,779 | B2 | 5/2008 | Chen et al. |
| 7,384,653 | B2 | 6/2008 | Wright et al. |
| 7,476,402 | B2 | 1/2009 | Kumar et al. |
| 7,510,726 | B2 | 3/2009 | Kumar et al. |
| 7,524,515 | B2 | 4/2009 | Roberts |
| 7,611,728 | B2 | 11/2009 | Kidane |
| 7,674,799 | B2 | 3/2010 | Chapman et al. |
| 7,674,800 | B2 | 3/2010 | Chapman et al. |
| 7,683,072 | B2 | 3/2010 | Chapman et al. |
| 7,776,314 | B2 | 8/2010 | Bartholamaus et al. |
| 7,879,352 | B2 | 2/2011 | Solomon et al. |
| 7,897,179 | B2 | 3/2011 | Mulye |
| 7,906,143 | B1 | 3/2011 | Odidi |
| 8,114,383 | B2 | 2/2012 | Bartholomaus et al. |
| 8,273,798 | B2 | 9/2012 | Bausch et al. |
| 8,389,007 | B2 | 3/2013 | Wright et al. |
| 8,420,700 | B1 | 4/2013 | Bausch et al. |
| 9,101,636 | B2 | 8/2015 | Brzeczko et al. |
| 9,101,817 | B2 | 8/2015 | Doerksen |
| 9,320,796 | B2 | 4/2016 | Brzeczko et al. |
| 9,662,393 | B2 | 5/2017 | Brzeczko et al. |
| 10,083,794 | B2 | 9/2018 | Sano et al. |
| 10,441,657 | B2 | 10/2019 | Brzeczko et al. |
| 10,688,184 | B2 | 6/2020 | Brzeczko et al. |
| 11,083,794 | B2 | 8/2021 | Brzeczko et al. |
| 2002/0022057 | A1 | 2/2002 | Battey |
| 2002/0119196 | A1 | 8/2002 | Parikh |
| 2003/0004177 | A1 | 1/2003 | Kao et al. |
| 2003/0021841 | A1 | 1/2003 | Matharu |
| 2003/0039691 | A1 | 2/2003 | Waterman |
| 2003/0049272 | A1 | 3/2003 | Joshi et al. |
| 2003/0049320 | A1 | 3/2003 | Bhagwatwar |
| 2003/0050620 | A1 | 3/2003 | Odidi |
| 2003/0059471 | A1 | 3/2003 | Compton |
| 2003/0064099 | A1 | 4/2003 | Oshlack et al. |
| 2003/0064122 | A1 | 4/2003 | Goldberg et al. |
| 2003/0068276 | A1 | 4/2003 | Hughes et al. |
| 2003/0068370 | A1 | 4/2003 | Sackler et al. |
| 2003/0068371 | A1 | 4/2003 | Oshlack et al. |
| 2003/0068375 | A1 | 4/2003 | Wright et al. |
| 2003/0068392 | A1 | 4/2003 | Sackler et al. |
| 2003/0096791 | A1 | 5/2003 | Gupte |
| 2003/0099711 | A1 | 5/2003 | Meadows |
| 2003/0124061 | A1 | 7/2003 | Roberts et al. |
| 2003/0124185 | A1 | 7/2003 | Oshlack et al. |
| 2003/0125347 | A1 | 7/2003 | Anderson et al. |
| 2003/0170181 | A1 | 9/2003 | Midha |
| 2003/0180362 | A1 | 9/2003 | Park |
| 2003/0232081 | A1 | 12/2003 | Doshi et al. |
| 2004/0081695 | A1 | 4/2004 | Sowden |
| 2004/0109889 | A1 | 6/2004 | Bunick |
| 2004/0131552 | A1 | 7/2004 | Boehm |
| 2004/0151791 | A1 | 8/2004 | May-Alvarez et al. |
| 2004/0185097 | A1 | 9/2004 | Kannan |
| 2004/0228802 | A1 | 11/2004 | Chang et al. |
| 2004/0265372 | A1 | 12/2004 | Wynn et al. |
| 2005/0013857 | A1 | 1/2005 | Fu |
| 2005/0020613 | A1 | 1/2005 | Boehm et al. |
| 2005/0063909 | A1 | 3/2005 | Wright et al. |
| 2005/0106249 | A1 | 5/2005 | Hwang et al. |
| 2005/0112067 | A1 | 5/2005 | Kumar et al. |
| 2005/0163851 | A1 | 7/2005 | Feleder |
| 2006/0003007 | A1 | 1/2006 | Odidi et al. |
| 2006/0008527 | A1 | 1/2006 | Lagoviyer |
| 2006/0013876 | A1 | 1/2006 | Lohray |
| 2006/0018837 | A1 | 1/2006 | Preston et al. |
| 2006/0029661 | A1 | 2/2006 | Radhakruhnan |
| 2006/0057210 | A1 | 3/2006 | Oshlack et al. |
| 2006/0093631 | A1 | 5/2006 | Buehler |
| 2006/0110327 | A1 | 5/2006 | Emigh et al. |
| 2006/0177380 | A1 | 8/2006 | Emigh et al. |
| 2007/0042044 | A1 | 2/2007 | Fischer et al. |
| 2007/0065510 | A1 | 3/2007 | Odidi et al. |
| 2007/0134493 | A1 | 6/2007 | Meghpara |
| 2007/0215511 | A1 | 9/2007 | Mehta |
| 2007/0292510 | A1 | 12/2007 | Huang |
| 2008/0014228 | A1 | 1/2008 | Darmuzey |
| 2008/0095843 | A1 | 4/2008 | Nutalapati |
| 2008/0152595 | A1 | 6/2008 | Emigh et al. |
| 2008/0260837 | A1 | 10/2008 | Namburi |
| 2008/0287456 | A1 | 11/2008 | Roberts |
| 2008/0305166 | A1 | 12/2008 | Durig |
| 2008/0312168 | A1 | 12/2008 | Pilgaonkar et al. |
| 2008/0312264 | A1 | 12/2008 | Arkenau-Maric et al. |
| 2008/0317854 | A1 | 12/2008 | Arkenau et al. |
| 2009/0004281 | A1 | 1/2009 | Nghiem |
| 2009/0005408 | A1 | 1/2009 | Arkena-Maric et al. |
| 2009/0081290 | A1 | 3/2009 | McKenna et al. |
| 2009/0081291 | A1 | 3/2009 | Gin |
| 2009/0098200 | A1 | 4/2009 | Krayz et al. |
| 2009/0142378 | A1 | 6/2009 | Frisbee |
| 2009/0175937 | A1 | 7/2009 | Rahmouni et al. |
| 2009/0202634 | A1 | 8/2009 | Jans et al. |
| 2009/0208572 | A1 | 8/2009 | Dharmadhikari et al. |
| 2009/0208576 | A1 | 8/2009 | Gandhi |
| 2009/0232887 | A1 | 9/2009 | Odidi et al. |
| 2009/0311327 | A1 | 12/2009 | Roberts |
| 2009/0317355 | A1 | 12/2009 | Roth et al. |
| 2010/0010101 | A1 | 1/2010 | Cherukuri |
| 2010/0015223 | A1 | 1/2010 | Cailly-Dufestel et al. |
| 2010/0015224 | A1 | 1/2010 | Singh |
| 2010/0092555 | A1 | 4/2010 | Wynn |
| 2010/0099696 | A1 | 4/2010 | Soscia et al. |
| 2010/0151028 | A1 | 6/2010 | Ashworth et al. |
| 2010/0249045 | A1 | 9/2010 | Babul |

(56) References Cited

U.S. PATENT DOCUMENTS

| | | | |
|---|---|---|---|
| 2010/0255063 | A1 | 10/2010 | Andersen |
| 2010/0260842 | A1 | 10/2010 | Nair |
| 2010/0266666 | A1 | 10/2010 | Andersen |
| 2010/0297031 | A1 | 11/2010 | Ubeda Perez et al. |
| 2010/0330150 | A1 | 12/2010 | Venkatesh |
| 2011/0020440 | A1 | 1/2011 | Modi |
| 2011/0028456 | A1 | 2/2011 | Lulla |
| 2011/0077238 | A1 | 3/2011 | Leech |
| 2011/0207761 | A1 | 8/2011 | Losev et al. |
| 2013/0065885 | A1 | 3/2013 | Roberts et al. |

METHODS AND COMPOSITIONS FOR SELF-REGULATED RELEASE OF ACTIVE PHARMACEUTICAL INGREDIENT

CROSS-REFERENCE TO RELATED APPLICATIONS

This application is a continuation of U.S. patent application Ser. No. 17/366,256 filed on Jul. 2, 2021, now U.S. Pat. No. 11,857,629, which is a continuation of U.S. patent application Ser. No. 16/899,529 filed on Jun. 11, 2020, now U.S. Pat. No. 11,083,794, which is a continuation of U.S. patent application Ser. No. 16/041,331 filed on Jul. 20, 2018, now U.S. Pat. No. 10,688,184, which is a divisional of U.S. patent application Ser. No. 15/588,982 filed May 8, 2017, now U.S. Pat. No. 10,441,657, which is a continuation of U.S. patent application Ser. No. 15/074,458 filed Mar. 18, 2016, now U.S. Pat. No. 9,662,393, which is a continuation of U.S. patent application Ser. No. 14/790,113 filed Jul. 2, 2015, now U.S. Pat. No. 9,320,796, which is a continuation of U.S. patent application Ser. No. 14/091,817 filed Nov. 27, 2013, now U.S. Pat. No. 9,101,636, and claims benefit of US Provisional Patent Appln. No. 61/731,901, filed Nov. 30, 2012. The entireties of these applications are hereby incorporated by reference herein.

BACKGROUND OF THE INVENTION

The class of drugs exhibiting opium or morphine-like properties are referred to as opioids, or opioid agonists. As agonists, certain thugs are characterized as interacting with stereo specific and saturable binding sites in the brain and other body tissues and organs. Endogenous opioid-like peptides are present in areas of the central nervous system that are presumed to be related to the perception of pain; to movement, mood and behavior; and to the regulation of neuroendocrinological functions. Three classical opioid receptor types, mu (μ), delta (δ), and kappa (κ), have been studied extensively. Each of these receptors has a unique anatomical distribution in the brain, spinal cord, and the periphery. Most of the clinically used opioids are relatively selective for μ receptors, reflecting their similarity to morphine. However, opioid containing drugs that are relatively selective for a particular receptor subtype at standard therapeutic doses will often interact with multiple receptor subtypes when given at sufficiently high doses, leading to possible changes in their pharmacological effect. This is especially true as opioid doses are escalated to overcome tolerance.

The potential for the development of tolerance, physical and/or psychological dependence (i.e., addiction) with repeated opioid use is a characteristic feature of most drugs containing opioid analgesics. The possibility of developing addiction is one of the major concerns in the use of opioids for the management of pain. Another major concern associated with the use of opioids is the diversion of these drugs from a patient in legitimate pain to other individuals (non-patients) for recreational purposes.

Drug abusers and/or addicts typically may take a solid dosage form intended for oral administration containing one or more opioid analgesics and crush, shear, grind, chew, dissolve and/or heat, extract or otherwise tamper with or damage the dosage unit so that a significant portion or even the entire amount of the active drug becomes available for administration by 1) injection, 2) inhalation, and/or 3) oral consumption in amounts exceeding the typical therapeutic dose for such drugs.

There are three basic patterns of behavior leading to opioid abuse. The first involves individuals whose opioid drug use begins in the context of legitimate medical treatment and who obtain their initial drug supplies through prescriptions from appropriately licensed health care providers. Through an insidious process these individuals may ultimately begin seeking prescription drug supplies far exceeding their legitimate medical needs from multiple health care providers and/or pharmacies and/or from illicit sources diverted from otherwise legal drug distribution channels. The second pattern of abuse begins with experimental or "recreational" drug users seeking a "high" with no legitimate medical indication for drugs subject to abuse. A third pattern of abuse involves users who begin in one or another of the preceding ways and ultimately switch to orally administered drugs obtained from organized and legitimate addiction treatment programs.

There are various routes of administration an abuser may commonly employ to abuse an opioid containing drug formulation. The most common methods include 1) parenteral intravenous injection), 2) intranasal (e.g., snorting), and 3) repeated oral ingestion of excessive quantities, for example, of orally administered tablets or capsules. One mode of abuse of oral solid drugs involves the extraction of the opioid component from the dosage form by first mixing the dosage form with a suitable solvent (e.g., water), and then subsequently extracting the opioid component from the mixture for use in a solution suitable for intravenous injection of the opioid to achieve a "high."

Attempts have been made to diminish the abuse potential of orally administered drugs. These attempts generally centered on the inclusion in the oral dosage form of an antagonist which is not orally active but which will substantially block the effects of the drug if one attempts to dissolve the drug and administer it parenterally.

Despite all attempts, the misuse and abuse of pharmaceutical products continues to increase. Clearly there is a growing need for novel and effective methods and compositions to deter abuse of pharmaceutical products (e.g., orally administered pharmaceutical products) including but not limited to immediate release, sustained or extended release and delayed release formulations for drugs subject to abuse. In particular, such methods and compositions would be useful for opioid analgesics, for patients seeking drug therapy, which deter abuse and minimizes or reduces the potential for physical or psychological dependency.

SUMMARY OF THE INVENTION

According to some embodiments of the present invention, an abuse deterrent pharmaceutics) composition includes a pharmaceutically active ingredient; an acid soluble ingredient; and a buffering ingredient. In some embodiments, the acid soluble ingredient and the buffering ingredient retard release of the pharmaceutically active ingredient when the composition is ingested in excess of an intended dosage.

In some embodiments, the pharmaceutically active ingredient is a drug susceptible to abuse. In some embodiments, the pharmaceutically active ingredient is a drug having a narrow therapeutic index.

In some embodiments, the acid soluble ingredient may include calcium carbonate, cationic copolymer, or combinations thereof. In certain embodiments, the acid soluble ingredient includes a cationic copolymer based on dimethylaminoethyl methacrylate, butyl methacrylate, and methyl methacrylate. The acid soluble ingredient may be present in an amount of about 1 wt % to about 40 wt % of the pharmaceutical composition.

In some embodiments, the pharmaceutically active ingredient is contained within a matrix of the acid soluble ingredient.

In certain embodiments, the buffering ingredient may include calcium carbonate, sodium bicarbonate, magnesium oxide, tribasic sodium phosphate, or combinations thereof. The buffering ingredient may be present in an amount of about 45 wt % to about 95 wt %.

BRIEF DESCRIPTION OF THE DRAWINGS

The present invention will be better understood by examining the following figures which illustrate certain properties of the present invention wherein.

With reference to the Figures, features that are the same across the Figures are denoted with the same reference numbers.

DETAILED DESCRIPTION OF THE INVENTION

Figure 1:
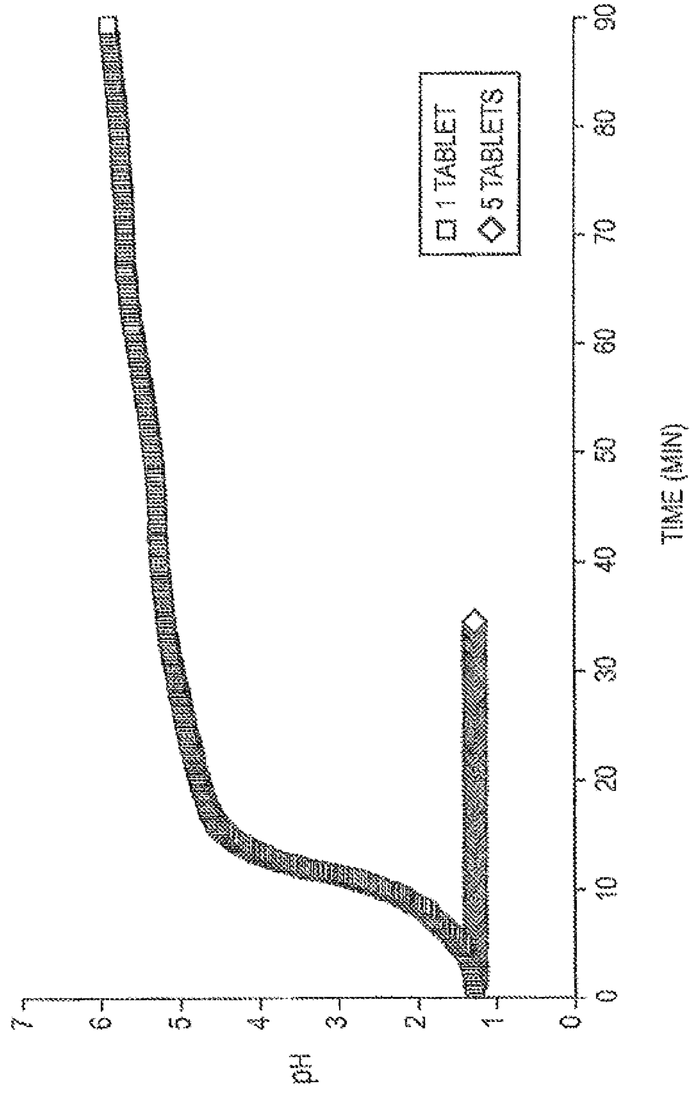
FIG. 1 shows the effect of calcium carbonates on pH of a dissolution medium over time.

In some embodiments, formulations of the present invention are designed to block or thwart the effects caused by intentional or unintentional over-ingestion of drug products. Under normal dosing conditions the inventive formulations may allow for the complete and/or bioequivalent oral delivery of the desired drug dose. However when excess doses am ingested, either intentionally or unintentionally, the inventive formulations may work to either slow or block the release and subsequent absorption of the excessive doses. Thus, in the case of intentional over-ingestion where a drug abuser would consume excess doses of an abused drug to experience a euphoric effect, the effect would be significantly reduced for the inventive formulations compared to doses which freely release the excess drug of abuse. In this way, the inventive formulation may work as a deterrent from abusing the inventive formulations for the purpose of achieving the euphoric effect. Yet the patient who uses the invention as directed will receive the desired therapeutic treatment.

In general, and as described in more detail herein, pharmaceutical formulations of the present invention may be designed with one or more components to control release and/or absorption of an active pharmaceutical ingredient. In some embodiments, a pharmaceutical formulation may be designed with a pH modifying, feature and/or a pH dependent solubility feature. A pH modifying feature may impact release and/or absorption of an active ingredient by modifying the pH of the gastric environment based on whether the pharmaceutical composition is taken at an appropriate dosage amount or in excess. A pH modifying feature may be provided by inclusion of one or more buffering and/or antacid ingredients in the pharmaceutical composition. A pH dependent solubility feature may impact release and/or absorption of an active ingredient by containing or releasing the active pharmaceutical ingredient, depending on the pH of the gastric environment. A pH dependent solubility feature may be provided by inclusion of one or more acid soluble ingredients in the pharmaceutical composition.

Components

Active Pharmaceutical Ingredients

Any drug, therapeutically acceptable drug salt, drug derivative, drug analog, drug homologue, or polymorph can be used in the present invention. Suitable drugs for use with the present invention can be found in the Physician's Desk Reference, 59th Edition, the content of which is hereby incorporated by reference. In one embodiment, the drug is an orally administered drug.

In certain embodiments, drugs susceptible to abuse are used. Drugs commonly susceptible to abuse include psychoactive drugs and analgesics, including but not limited to opioids, opiates, stimulants, tranquilizers, sedatives, anxiolytics, narcotics and drugs that can cause psychological and/or physical dependence. In one embodiment, the drug for use in the present invention can include amphetamines, amphetamine-like compounds, benzodiazepines, and methyl phenidate or combinations thereof. In another embodiment, the present invention can include any of the resolved isomers of the drugs described herein, and/or salts thereof.

A drug for use in the present invention which can be susceptible to abuse can be one or More of the following: alfentanil, amphetamines, buprenorphine, butorphanol, carfentanil, codeine, dezocine, diacetylmorphine, dihydrocodeine, dihydromorphine, diphenoxylate, diprenorphine, etorphine, fentanyl, hydrocodone, hydromorphone, β-hydroxy-3-methylfentanyl, levo-α-acetylmethadol, levorphanol, lofentanil, meperidine, methadone, methylphenidate, morphine, nalbuphine, nalmefene, oxycodone, oxymorphone, pentazocine, pethidine, propoxyphene, remifentanil, sufentanil, tilidine, and tramodol, salts, derivatives, analogs, homologues, polymorphs thereof, and mixtures of any of the foregoing.

In another embodiment a drug for use with the present invention which can be susceptible to abuse includes one or more of the following: dextromethorphan (3-Methoxy-17-methy-9a, 13a, 14a-morphinan hydrobromide monohydrate), N-{1-[2-(4-ethyl-5-oxo-2-tetrazolin-1-yl)-ethyl]-4-methoxymethyl-4-piperidyl} propionanilide (alfentanil), 5,5-diallyl barbituric acid (allobarbital), allylprodine, alphaprodine, 8-chloro-1-methyl-6-phenyl-4H-[1,2,4]triazolo[4,3-a][1,4]-benzodiazepine (alprazolam), 2-diethyluminopropiophenone (amfepramone), (±)-α-methyl phenethylamine (amphetamine), 2-(α-methylphenethyl-amino)-2-phenyl acetonitrile (amphetaminil), 5-ethyl-5-isopentyl barbituric acid (amobarbital), anileridine, apocodeine, 5,5-diethyl barbituric acid (barbital), benzylmorphine, bezitramide, 7-bromo-5-(2-pyridyl)-1H-1,4-benzodiazepin-2(3H)-one (bromazepam), 2-bromo-4-(2-chlorophenyl)-9-methyl-6H-thieno[3,2-f][1,2,4]-triazolo[4,3-a][1,4]diazepine (brotizolam), 17-cyclopropylmethyl-4,5α-epoxy-7α[(S)-1-hydroxy-1,2,2-trimethylpropyl]-6-methoxy-6,14-endo-ethanomorphinan-3-ol (buprenorphine), 5-butyl-5-ethyl barbituric acid (butobarbital), butorphanol, (7-chloro-1,3-dihydro-1-methyl-2-oxo-5-phenyl-2H-1,4-benzodiazepin-3-yl)-dimethyl carbamate (camazepam), (1S,2S)-2-amino-1-phenyl-1-propanol (cathine/D-norpseudoephedrine), 7-chloro-N-methyl-5-phenyl-3H-1,4-benzodiazepin-2-ylamine-4 oxide (chlordiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepin-2

(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]-diazepin-2(3H)-one (clotiazepam), 10-chloro-11b-(2-chlorophenyl)-2,3,7,11b-tetrahydrooxazolo[3,2-d][1,4]benzodiazepin-6(5H)-one (claxazolam), (−)-methyl-[3β-benzoyloxy-2β(1αH,5αH)-tropane carboxylate (cocaine), 4,5α-epoxy-3-methoxy-17-methyl-7-morphinen-6α-ol (codeine), 5-(1-cyclohexenyl)-5-ethyl barbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl) propionate (dextropropoxyphene), dezocine, diampromide, diamorphone, 7-chloro-1-methyl-5-phenyl-1H-1,4-benzediazepin-2(3H)-one (diazepam), 4,5α-epoxy-3-methoxy-17-methyl-6α-morphinanol (dihydrocodeine), 4,5α-epoxy-7-methyl-3,6a-morphinandiol(dihydromorphine), dimenoxadol, dimephetamol [sic-Tr.Ed], dimethyl thiambutene, dioxaphetyl butyrate, dipipanone, (6aR,10aR)-6,6,9-trimethyl-3-pentyl-6a,7,8,10a-tetrahydro-6H-benzo[c]chromen-1-ol (dronabinol), eptazocine, 8-chloro-6-phenyl-4H-[1,2,4]triazolo[4,3-a][1,4]benzodiazepine (estazolam), ethoheptazine, ethyl methyl thiambutene, ethyl-[7-chloro-5-(2-fluorophenyl)-2,3-dihydro-2-oxo-1H-1,4-benzodiazepin-3-carboxylate] (ethyl loflazepate), 4,5α-epoxy-3-ethoxy-17-methyl-7-morphinen-6α-ol (ethylmorphine), etonitrazene, 4,5α-epoxy-7α-(1-hydroxy-1-methylbutyl)-6-methoxy-17-methyl-6,14-endo-etheno-morphinan-3-ol (etorphine), N-ethyl-3-phenyl-8,9,10-trinorbornan-2-ylamine (fencamfamine), 7-[2-(α-methylphenethylamino)-ethyl] theophylline (fenethylline), 3-(α-methylphenethylamino) propionitrile (fenproporex), N-(1-phenethyl-4-piperidyl) propionanilide (fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2-(3H)-one (flunitrazepam), 7-chloro-1-(2-diethylaminoethyl)-5-(2-fluorophenyl)-1H-1,4-benzodiazepin-2(3H)-one (flurazepam), 7-chloro-5-phenyl-1-(2,2,2-trifluoroethyl)-1H-1,4-benzodiazepin-2(3H)-one (halazepam), 10-bromo-11b-(2-fluorophenyl)-2,3,7,11b-tetrahydro[1,3]oxazolo[3,2-d][1,4]benzodiazepin-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethyl morphinan, 11-chloro-8,12b-dihydro-2,8-dimethyl-12b-phenyl-4H-[1,3]oxazino[3,2-d][1,4]benzodiazepin-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenylheptan-3-yl acetate (levacetylmethadol(LAAM)), (−)-6-dimethylamino-4,4-diphenyl-3-heptanone (levomethadone), (−)-17-methyl-3-morphinanol (levorphanol), levophenacyl morphan, lofentanil, 6-(2-chlorophenyl)-2-(4-methyl-1-piperazinylmethylene)-8-nitro-2H-imidazo[1,2a][1,4]benzodiazepin-1(4H)-one (loprazolam), 7-chloro-5-(2-chlorophenyl)-3-hydroxy-1H-1,4-benzodiazepin-2(3H)-one (lorazepam), 7-chloro-5-(2-chlorophenyl)-3-hydroxy-1-methyl-1H-1,4-benzodiazepin-2(3H)-one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenetylamine (mefenorex), meperidine, 2-methyl-2-propyl trimethylene dicarbamate (meprobamate), meptazinol, metazocine, methylmorphine, N,α-dimethylphenethylamine (methamphetamine), (±)-6-dimethylamino-4,4-diphenyl-3-heptanone (methadone), 2-methyl-3-o-tolyl-4(3H)-quinazolinone (methaqualone), methyl-[2-phenyl-2-(2-piperidyl)acetate] (methyl phenidate), 5-ethyl-1-methyl-5-phenyl barbituric acid (methyl phenobarbital), 3,3-diethyl-5-methyl-2,4-piperidinedione (methyprylon), metopon, 8-chloro-6-(2-fluorophenyl)-1-methyl-4H-imidazo[1,5-a][1,4]benzodiazepine (midazolam), 2-(benzhydrylsuflinyl) acetamide (modafinil), 4,5α-epoxy-17-methyl-7-morphinene-3,6α-diol (morphine), myrophine, (±)-trans-3-(1,1-dimethylheptyl)-7,8,10,10α-tetrahydro-1-hydroxy-6,6-dimethyl-6H-dibenzo[b,d]pyran-9(6αH)-one (nabilone), nalbuphen, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one (nitrazepam), 7-chloro-5-phenyl-1H-1,4-benzodiazepin-2-(3H)-one (nordazepam), norlevorphanol, 6-dimethylamino-4,4-diphenyl-3-hexanone (normethadone), normorphine, norpipanone, the coagulated juice of the plants belonging to the species *Papaver somniferum* (opium), 7-chloro-3-hydroxy-5-phenyl-1H-1,4-benzodiazepin-2-(3H)-one (oxazepam), (cis-trans)-10-chloro-2,3,7,11b-tetrahydro-2-methyl-11b-phenyloxazolo[3,2-d][1,4]benzodiazepin-6-(5H)-one (oxazolam), 4,5α-epoxy-14-hydroxy-3-methoxy-17-methyl-6-morphinanone (oxycodone), oxymorphone, plants and plant parts of the plants belonging to the species *Papaver somniferum* (including the subspecies *setigerum*) (*Papaver somniferum*), papaveretum, 2-imino-5-phenyl-4-oxazolidinone (pernoline), 1,2,3,4,6-hexahydro-6,11-dimethyl-3-(3-methyl-2-butenyl)-2,6-methano-3-benzazocin-8-ol (pentazocine), 5-ethyl-5-(1-methylbutyl) barbituric acid (pentobarbital), ethyl-(1-methyl-4-phenyl-4-piperidine-carboxylate) (pethidine), phenadoxone, phenomorphan, phenazocine, phenoperidine, piminodine, pholcodeine, 3-methyl-2-phenyl morpholine (phenmetrazine), 5-ethyl-5-phenyl barbituric acid (phenobarbital), α,α-dimethyl phenethylamine (phentermine), 7-chloro-5-phenyl-1-(2-propinyl)-1H-1,4-benzodiazepin-2(3H)-one (pinazepam), α-(2-piperidyl)benzhydryl alcohol (pipradol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepin-2(3H)-one (prazepam), profadol, proheptazine, promedol, properidine, propoxyphene, N-(1-methyl-2-piperidinoethyl)-N-(2-pyridyl) propionamide, methyl-{3-[4-methoxycarbonyl-4-(N-phenylpropaneamido)piperidino]propanoate} (remifentanil), 5-sec.-butyl-5-ethyl barbituric acid (secbutabarbital), 5-allyl-5-(1-methylbutyl) barbituric acid (secobarbital), N-{4-methoxymethyl-1-[2-(2-thienyl)ethyl]-4-piperidyl} propionanilide (sufentanil), 7-chloro-2-hydroxy-methyl-5-phenyl-1H-1,4-benzodiazepin-2-(3H)-one (temazepam), 7-chloro-5-(1-cyclohexenyl)-1-methyl-1H-1,4-benzodiazepin-2(3H)-one (tetrazepam), ethyl-(2-dimethylamino-1-phenyl-3-cyclohexane-1-carboxylate) (tilidine (cis and trans)), tramadol, 8-chloro-6-(2-chlorophenyl)-1-methyl-4H-[1,2,4]triazolo[4,3-a][1,4]benzodiazepine (triazolam), 5-(1-methylbutyl)-5-vinyl barbituric acid (vinylbital), (1R*,2R*)-3-(3-dimethylamino-1-ethyl-2-methyl-propyl) phenol, (1R,2R,4S)-2-[dimethylamino)methyl-4-(p-fluorobenzyloxy)-1-(m-methoxyphenyl) cyclohexanol, each optionally in the form of corresponding stereoisomeric compounds as well as corresponding derivatives, especially esters or ethers, and all being physiologically compatible compounds, especially salts and solvates.

In one embodiment, a pharmaceutical composition of the present invention includes one or more opioids such as hydrocodone, hydromorphone, morphine and oxycodone and/or salts thereof, as the therapeutically active ingredient. Typically when processed into a suitable dosage form, as described in more detail below, the drug can be present in such dosage forms in an amount normally prescribed, typically about 0.5 to about 25 percent on a dry weight basis, based on the total weight of the formulation.

With respect to analgesics in unit dose form, such drugs may be present in a pharmaceutically acceptable amount; standard doses of such drugs are generally known in the art and are disclosed, for example, in the *United States Pharmacopeia and National Formulary* (USP 36-NF 31). Rockville, MD: United States Pharmacopeia. Convention; 2013, Which is incorporated by reference herein in its entirety. In some embodiments, such drugs may be present in an amount of about 5, 25, 50, 75, 100, 125, 150, 175 or 200 mg. In some embodiments, the drug can be present in an amount from about 5 to about 500 mg or about 5 to about 200 mg. In some embodiments, a dosage form contains an appropriate amount of drug to provide a therapeutic effect.

In some embodiments, a pharmaceutically active ingredient may include a drug having a narrow therapeutic index. Drugs having a narrow therapeutic index may include but are not limited to aminophylline, carbamazepine, clindamycin, clonidine, digoxin, disopyramide, dyphylinne, guanthidine, isoetharine mesylate, isoproterenol, levothyroxine, lithium carbonate, metaproterenol, minoxidil, oxytriphylline, phenytoin, pasosin, primidone, procainamide, quinidine gluconate, theophylline, valproic acid, valproate sodium and warfarin sodium and the like. With respect to drugs having a narrow therapeutic dose in unit dose form, such drugs may be present in a pharmaceutically acceptable amount; standard doses of such drugs are generally known in the art and are disclosed, for example, in the *United States Pharmacopeia and National Formulary* (USP 36-NF 31). Rockville, MD; United States Pharmacopeia Convention; 2013, which is incorporated by reference herein in its entirety. In some embodiments, such drugs may be present in an amount of about 0.025, 0.05, 0.1, 0.2, 0.3, 0.5, 1, 2, 2.5, 3, 4, 5, 6, 7.5, 10, 25, 50, 75, 100, 125, 150, 175, 200, and 250 mg. In some embodiments, the drug can be present in an amount of from about 0.01 to about 1000 mg or about 0.05 to about 500 mg. In some embodiments, a dosage form contains an appropriate amount of drug to provide a therapeutic effect.

Component Soluble in Acidic Solutions

In some embodiments, pharmaceutical compositions of the present invention include one or more components which are soluble in acidic solutions. Acidic solutions may be considered those having a pH of about 1 to about 4. In some embodiments, the acid soluble component is less soluble in slightly acidic, neutral, and/or basic solutions, i.e., those having a pH of greater than about 4.

In some embodiments, an acid soluble component is included in a pharmaceutical composition in the form of particle matrix with an active pharmaceutical ingredient. The acid soluble ingredient may be included in the pharmaceutical composition in an amount sufficient to form this matrix. In some embodiments, the active ingredient is sequestered within the acid soluble component. The acid soluble component may impact release of the active pharmaceutical ingredient depending on the pH of the environment, which is raised or maintained by the buffering and/or antacid ingredient as a function of the amount of the pharmaceutical composition ingested: when the pharmaceutical composition is invested in an appropriate dosage amount, the pH buffering ingredient is not present in an amount to alter or sufficiently raise the gastrointestinal and the acid soluble component dissolves and releases the active pharmaceutical ingredient; when the pharmaceutical component is ingested in an excess amount, the pH buffering ingredient is present in an amount to raise the gastrointestinal pH, thereby preventing the acid soluble ingredient from dissolving and releasing the active pharmaceutical ingredient.

In some embodiments, an acid soluble component is included in the pharmaceutical composition an amount of about 1 wt % to about 50 wt %; about 1 wt % to about 48 wt %; about 1 wt % to about 46 wt %; about 1 wt % to about 44 wt %; about 1 wt % to about 42 wt %; about 1 wt % to about 40 wt %; about 2 wt % to about 38 wt %; about 4 wt % to about 36 wt %; about 6 wt % to about 34 wt %; about 8 wt % to about 32 wt %; about 10 wt % to about 30 wt %; about 12 wt % to about 28 wt %; about 14 wt % to about 26 wt %; about 16 wt % to about 24 wt %; about 18 wt % to about 22 wt %; about 1 wt %; about 2 wt %; about 4 wt %; about 6 wt %; about 8 wt %; about 10 wt %; about 12 wt %; about 14 wt %; about 16 wt %; about 18 wt %; about 20 wt %; about 22 wt %; about 24 wt %; about 26 wt %; about 28 wt %; about 30 wt %; about 32 wt %; about 34 wt %; about 36 wt %; about 38 wt %; about 40 wt %; about 42 wt %; about 44 wt %; about 46 wt %; about 48 wt %; or about 50 wt %.

Examples of suitable acid soluble components include calcium carbonate, chitosan, cationic copolymers of dimethylaminoethyl methacrylate, butyl methacrylate, and methyl methacrylate such as, for example, Eudragit® E PO Eudragit® E100 and Eudragit® E 12.5, di and tribasic calcium phosphate, and magnesium hydroxide.

Buffering and/or Antacid Ingredients

In some embodiments, pharmaceutical compositions of the present invention include one or more buffering and/or antacid ingredients. Such ingredient may result in an elevation in stomach pH if the pharmaceutical composition is consumed in adequate amounts. In some embodiments, such ingredient may result in rapid and sustained elevation of stomach pH to a pH of greater than about 4 when the pharmaceutical composition is consumed in adequate amounts.

In some embodiments, a buffering and/or antacid ingredient may be included in an amount such that stomach is not affected when the pharmaceutical composition is taken in appropriate therapeutic amounts, but such that stomach pH may be elevated when the pharmaceutical composition is ingested in excess amounts. In some embodiments, a buffering and/or antacid ingredient is included in the pharmaceutical composition in an amount of about 45 wt % to about 95 wt %; about 50 wt % to about 90 wt %; about 55 wt % to about 85 wt %; about 60 wt % to about 80 wt %; about 65 wt % to about 75 wt %; about 45 wt %; about 50 wt %; about 55 wt %; about 60 wt %; about 65 wt %; about. 70 wt %; about 75 wt %; about 80 wt %; about 85 wt %; about 90 wt %; or about 95 wt %.

Examples of suitable buffering and/or antacid ingredients include but are not limited to aluminum hydroxide, bismuth aluminate, bismuth carbonate, bismuth subcarbonate, bismuth subgallate, bismuth subnitrate, calcium carbonate, calcium phosphate, dibasic calcium phosphate, dihydroxyaluminum aminoacetate, dihydroxyaluminum sodium carbonate, glycine, magnesium glycinate, magnesium hydroxide, magnesium oxide, potassium bicarbonate, sodium bicarbonate, sodium potassium tartrate, tribasic sodium phosphate and tricalcium phosphate.

In some embodiments, one ingredient may act as both an acid soluble ingredient and a buffering and/or antacid ingredient. Examples of such suitable ingredients include calcium carbonate, di and tribasic calcium phosphate, and magnesium hydroxide.

Additional Ingredients

The present invention can also optionally include other ingredients to enhance dosage form manufacture from a pharmaceutical composition of the present invention and/or alter the release profile of a dosage form including a pharmaceutical composition of the present invention.

Some embodiments of the present invention include one or more pharmaceutically acceptable fillers/diluents. In one embodiment, Avicel PH (Microcrystalline cellulose) is a filler used in the formulation. The Avicel PH can have an average particle size ranging from 20 to about 200 μm, preferably about 100 μm. The density ranges from 1.512-1.668 g/cm$^3$. The Avicel PH should have molecular weight of about 36,000. Avicel PH effectiveness is optimal when it is present in an amount of from about 10 to 65 percent, by weight on a solid basis, of the formulation. Typical fillers can be present in amounts from 10 to 65 percent by weight on a dry weight basis of the total composition. Other ingredients can include sugars and/or polyols. Lactose having a particle size of about 20 to about 400 microns and a density of about 0.3 to about 0.9 g/ml can also be included.

In some embodiments of the invention, the fillers which can be present at about 10 to 65 percent by weight on a dry weight basis, also function as binders in that they not only impart cohesive properties to the material within the formulation, but can also increase the balk weight of a directly compressible formulation (as described below) to achieve an acceptable formulation weight for direct compression. In some embodiments, additional fillers need not provide the same level of cohesive properties as the binders selected, but can be capable of contributing to formulation homogeneity and resist segregation from the formulation once blended. Further, preferred fillers do not have a detrimental effect on the flowability of the composition or dissolution profile of the formed tablets.

In one embodiment, the present invention can include one or more pharmaceutically acceptable disintegrants. Such disintegrants are known to a skilled artisan. In the present invention, disintegrants can include, but are not limited to, sodium starch glycolate (Explotab®) having a particle size of about 104 microns and a density of about 0.756 g/ml, starch (e.g., Starch 21) having a particle size of about 2 to about 32 microns and a density of about 0.462 g/ml, Crospovidone® having a particle size of about 400 microns and a density of about 1.22 g/ml, and croscarmellose sodium (Ac-Di-Sol) having a particle size of about 37 to about 73.7 microns and a density of about 0.529 g/ml. The disintegrant selected should contribute to the compressibility, flowability and homogeneity of the formulation. Further the disintegrant can minimize segregation and provide an immediate release profile to the formulation. In some embodiments, the disintegrant(s) are present in an amount from about 2 to about 25 percent by weight on a solid basis of the directly compressible formulation. Furthermore, antacids added to the formulations may aid in tablet disintegration when the tablet is introduced to a low pH environment through the effervescence of the antacid ingredient, thus potentially reducing the requirement for additional disintegrants.

In one embodiment, the present invention can include one or more pharmaceutically acceptable glidants, including bat not limited to colloidal silicon dioxide. In one embodiment, colloidal silicon dioxide (Cab-O-Sil®) having a density of about 0.029 to about 0.040 g/ml can be used to improve the flow characteristics of the formulation. Such glidants can be provided in an amount of from about 0.1 to about 1 percent by weight of the formulation on a solid basis. It will be understood, based on this invention, however, that while colloidal silicon dioxide is one particular glidant, other glidants having similar properties which are known or to be developed could be used provided they are compatible with other excipients and the active ingredient in the formulation and which do not significantly affect the flowability, homogeneity and compressibility of the formulation.

In one embodiment, the present invention can include one or more pharmaceutically acceptable lubricants, including but not limited to magnesium stearate. In one embodiment, the magnesium stearate has a particle size of about 450 to about 550 microns and a density of about 1.00 to about 1.80 g/ml. In one embodiment, magnesium stearate can contribute to reducing friction between a die wall and a pharmaceutical composition of the present invention during compression and can ease the ejection of the tablets, thereby facilitating processing. In some embodiments, the lubricant resists adhesion to punches and dies and/or aid in the flow of the powder in a hopper and/or into a die. In an embodiment of the present invention, magnesium stearate having a particle size of from about 5 to about 50 microns and a density of from about 0.1 to about 1.1 g/ml is used in a pharmaceutical composition. In certain embodiments, a lubricant should make up from about 0.1 to about 2 percent by weight of the formulation on a solids basis. Suitable lubricants are stable and do not polymerize within the formulation once combined. Other lubricants known in the art or to be developed which exhibit acceptable or comparable properties include stearic acid, hydrogenated oils, sodium stearyl fumarate, polyethylene glycols, and Lubritab®.

In certain embodiments, the most important criteria for selection of the excipients are that the excipients should achieve good content uniformity and release the active ingredient as desired. The excipients, by having excellent binding properties, and homogeneity, as well as good compressibility, cohesiveness and flowability in blended form, minimize segregation of powders in the hopper during compression.

Controlled Drug Release Dosage Forms

As described herein, pharmaceutical formulations of the present invention may be formulated to slow or block the release and subsequent absorption of excessive doses of an active pharmaceutical ingredient. In some embodiments, a pharmaceutical formulation may be designed with a modifying feature and/or a pH dependent solubility feature. A pH modifying feature may impact release and/or absorption of an active ingredient by modifying the pH of the gastric environment based on whether the pharmaceutical composition is taken an appropriate dosage amount or in excess. A pH modifying feature may be provided by inclusion of one or more buffering and/or antacid ingredients in the pharmaceutical composition. A pH dependent solubility feature may impact release and/or absorption of an active ingredient by containing or releasing the active pharmaceutical ingredient, depending on the pH of the gastrointestinal environment. A pH dependent solubility feature may be provided by inclusion of one or more pH soluble ingredients in the pharmaceutical composition.

In some embodiments, the pharmaceutical composition may be formulated such that when the composition is taken in appropriate amounts, a pH modifying feature has minimal impact (i.e., the pH of the gastric environment is not substantially modified or is maintained at a desirable level) and a pH dependent solubility feature has a maximal impact (i.e., the active pharmaceutical ingredient is released), thereby allowing release and/or absorption of the active ingredient. However, when the pharmaceutical composition is ingested in excess, in some embodiments the composition is formulated such that the pH modifying feature has a maximal impact (i.e., the pH of the gastric environment is raised) and the pH dependent solubility feature has a minimal impact (i.e., the acid solubility ingredient is not soluble and therefore does not dissolve), thereby thwarting release and/or absorption of the active ingredient.

In some embodiment, a pharmaceutical composition may be prepared by intimately mixing the active pharmaceutical ingredient with an acid soluble ingredient(s) by any suitable process (i.e. dry or wet granulation, hot melt extrusion etc) such that a particulate matrix is formed in a particulate form. The release of the drug from this matrix may then be controlled by the immediate pH environment surrounding the matrix when the pharmaceutical composition is ingested. In a low pH environment (i.e., pH 1-4), the matrix may be likely to dissolve and release the drug rapidly; however, in a higher pH environment pH>4) the matrix is likely to be insoluble and the release of drug will be retarded and potentially incomplete, thereby diminishing the level of the drug absorbed.

In some embodiments, for a single dosage unit, the required amount of acid soluble drug matrix is further mixed with buffering and/or antacid ingredient(s) in a quantity sufficient such that when the single dose unit is ingested, the buffering and/or antacid ingredient(s) will neutralize stomach pH to a point that the stomach pH remains in a range between pH 1-4. The acid soluble drug matrix/antacid/buffer blend may be formed into an oral solid dose form such as a tablet or capsule hut not limited to said dosage forms.

As a result, a pharmaceutical composition may be formulated having a pH modifying feature and a pH dependant solubility feature such that, under normal dosing conditions (i.e., one or two tablets), when a single dose is ingested, the buffer/antacid ingredient(s) neutralize a portion of the stomach acid, however the stomach acid remains in a range between pH 1-4. Under these conditions, the acid soluble drug matrix is soluble in the acidic stomach environment and the drug may be rapidly released in the stomach and absorbed into the bloodstream.

Under conditions where excess doses are ingested, intentionally or unintentionally, (i.e., three tablets or greater), the quantity of buffers and/or antacid ingredient(s) from over-ingestion may now be sufficient to cause a rapid and sustainable increase in stomach pH (>pH 4), Thus the acid soluble drug matrix may be less soluble in the higher pH stomach environment and the release of drug from the matrix may be suppressed. In some embodiments, the suppression of drug from the acid soluble matrix is further aided by gastro-intestinal transit, which may transfer the acid soluble matrix particle into the intestine and lower gastro-intestinal tract which have biologically controlled high pH environments (i.e., pH 5.5-8). The overall suppression of drug release from over ingestion results in a pharmacokinetic profile with an increase in Tmax and a decrease in Cmax when compared to an equal oral dose which releases drug in normal stomach pH (i.e., pH 1-4).

Suitable formulations and dosage forms of the present invention include but are not limited to powders, caplets, pills, suppositories, gels, soft gelatin capsules, capsules and compressed tablets manufactured from a pharmaceutical composition of the present invention. The dosage forms can be any shape, including regular or irregular shape depending upon the needs of the artisan.

Compressed tablets including the pharmaceutical compositions of the present invention can be direct compression tablets or non-direct compression tablets. In one embodiment, a dosage form of the present invention can be made by wet granulation, and dry granulation (e.g., slugging or roller compaction). The method of preparation and type of excipients are selected to give the tablet formulation desired physical characteristics that allow for the rapid compression of the tablets. After compression, the tablets must have a number of additional attributes such as appearance, hardness, disintegrating ability, and an acceptable dissolution profile.

Choice of fillers and other excipients typically depend on the chemical and physical properties of the drug, behavior of the mixture during processing, and the properties of the final tablets. Adjustment of such parameters is understood to be within the general understanding of one skilled in the relevant art. Suitable fillers and excipients are described in more detail above.

The manufacture of a dosage form of the present invention can involve direct compression and wet and dry granulation methods, including slugging and roller compaction.

In some embodiments, one or more component may be sequestered, as described in U.S. Patent Application. Publication No. 2012/0202839 which is incorporated by reference herein in its entirety.

The present invention can be used to manufacture immediate release, and controlled drug release formulations. Controlled release formulations can include delayed release, hi-modal and tri-modal release, extended and sustained release oral solid dosage preparations.

As used herein, the term "about" is understood to mean ±10% of the value referenced. For example, "about 45%" is understood to literally mean 40.5% to 49.5%.

As used herein, the term "bioequivalence" is understood to mean one or more of $C_{max}$, $T_{max}$, or area under the concentration curve "AUC" of a drug is within 75% to 120% of the same marker for a referenced drug.

Certain aspects of the present invention may be better understood as illustrated by the following examples, which are meant by way of illustration and not limitation.

Example 1

Two dissolution vessels were prepared: one vessel contained 25 mEq of HCl and a single commercially available calcium carbonate antacid tablet (Tums®), and the other vessel contained 25 mEq of HCl and live calcium carbonate antacid tablets. The in each yeast was monitored and the results are shown in FIG. 1. For the single tablet, the tablet is completely reacted in about 30 minutes and the dissolution of the single tablet showed no change in pH. However, the introduction of five tablets results in a relatively rapid rise in 10 minutes to a pH greater than 4.5 and after 90 minutes, a considerable amount of non-dissolved solid was observed in the vessel. Therefore, it has been shown that calcium carbonate at a low level (500 mg) could completely dissolve with little effect on pH but with excess amounts of calcium carbonate a rapid pH increase occurs creating a high pH environment, in which calcium carbonate exhibits low solubility. Calcium carbonate has shown a capability as a pH modifier and pH dependent.

Example 2

Figure 2:
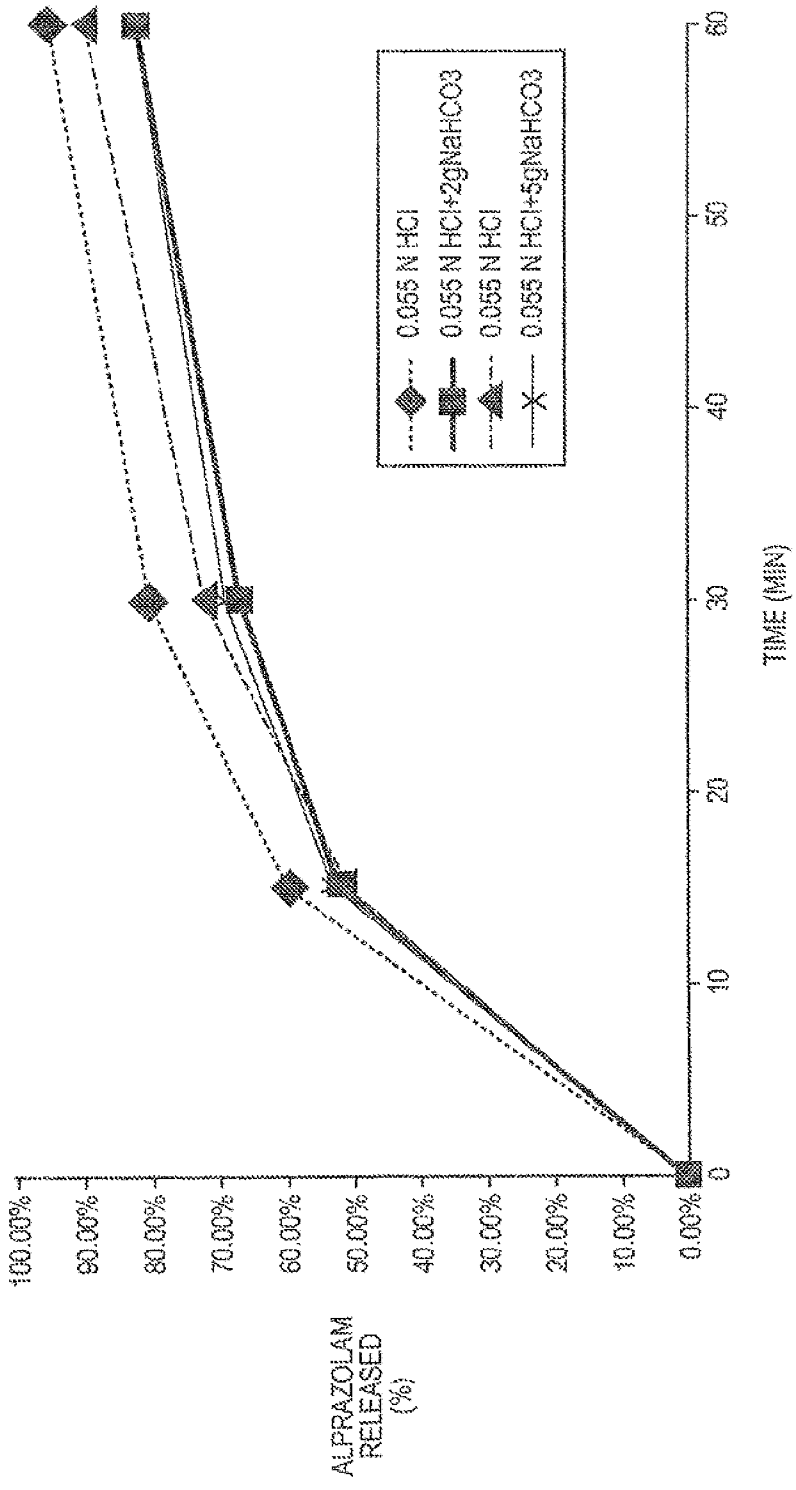
FIG. 2 shows the effect of dissolution medium on the release of an active ingredient from calcium carbonate granules.

A challenge faced in designing a self-regulating dosage form is to institute regulation (i.e., slower or incomplete release) at elevated pH without compromising the desired rapid release rate associated with immediate release tablets when a single dose is taken. Calcium carbonate was evaluated both in direct blend matrix tablets and dry granulation tablets containing alprazolam, where the granule contained calcium carbonate to control drug release and calcium carbonate outside the granule to effect pH change. Both approaches resulted in slower alprazolam release in single tablets at higher pH (approx. pH 6) compared to low pH (pH1), however, in this case the release separation was not as high as desired (FIG. 2), However, the results demonstrate that a granule may be used to control drug release depending on pH environment. The granules may consist of the drug along with a functional component that inhibits erosion or disintintegration at elevated pH such that slower and/or incomplete release of the drug is observed. The extragranular portion of the tablet may primarily contain the pH controlling agents, which need to be released and react quickly.

Example 3

Figure 3:
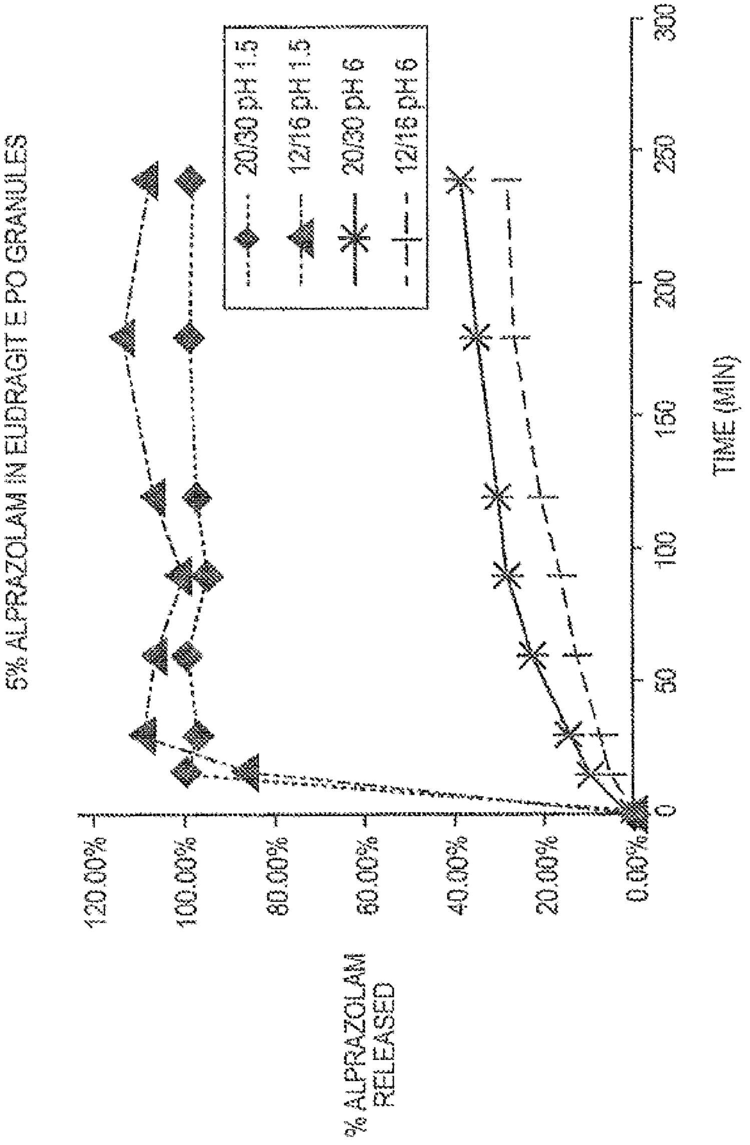
FIG. 3 shows the release of an active ingredient from cationic copolymer granules.

Eudragit® E PO (EPO) is a cationic copolymer based on dimethylaminoethyl methacrylate, butyl methacrylate, and methyl methacrylate. Technical literature indicates that this polymer is soluble in acid, up to pH 5; above pH 5 it swells rather than dissolves. Dry granulations containing 5% alprazolam in EPO polymer were prepared and size fractions collected at −16 mesh and +20 mesh (16/20) and at −20 mesh and +30 mesh (20/30). Dissolution on the granulation size fractions were performed at both low pH (pH 1.5) where EPO is soluble and at high pH (pH 6) were EPO is less soluble. The results are shown in FIG. 3. At low pH, irrespective of the particle size, a rapid and complete release of alprazolam occurs within 15 minutes. However at high pH, the release of alprazolam is significantly slower and incomplete for both size fractions but slightly elevated for the smaller fraction. It must be noted that this dissolution simulation represents a static pH condition at the potential pH extremes if the tablet is taken as directed (pH 1) and in excess (pH 6). The next example examines a pH modifying system which doesn't affect pH when taken as directed but will rapidly increase pH when over-ingested.

Example 4

Subsequent trials to use calcium carbonate as the primary pH modifying agent resulted in a relatively rapid release of alprazolam in 15 minutes from 5% alprazolam/EPO granules (60%). Although the change to pH 5 previously seen for calcium carbonate in 10 minutes (FIG. 1) may have been perceived Past, given that release of alprazolam is also rapid and completed in 15 minutes, calcium carbonate may not affect a pH change rapidly enough for the alprazolam/EPO granules. In earlier experimentation, sodium bicarbonate had been shown to have a more rapid pH effect, raising acid media from a pH 1 to a pH 6 in less than 2 minutes. Thus, sodium bicarbonate was added to a prototype formulation primarily to control rapid pH elevation and calcium carbonate for a more sustained control of elevated pH. A representative formulation for the invention is shown in the table below:

| Component | Wt % | Wt (mg) |
|---|---|---|
| Alprazolam (5%) in Eudragit E PO (20/30) | 3.195 | 20.00 |
| Sodium bicarbonate | 79.87 | 500.0 |
| Calcium carbonate DC | 15.97 | 100.0 |
| Magnesium stearate | 0.958 | 6.0 |
| Total | 100 | 626.0 |

Figure 4:
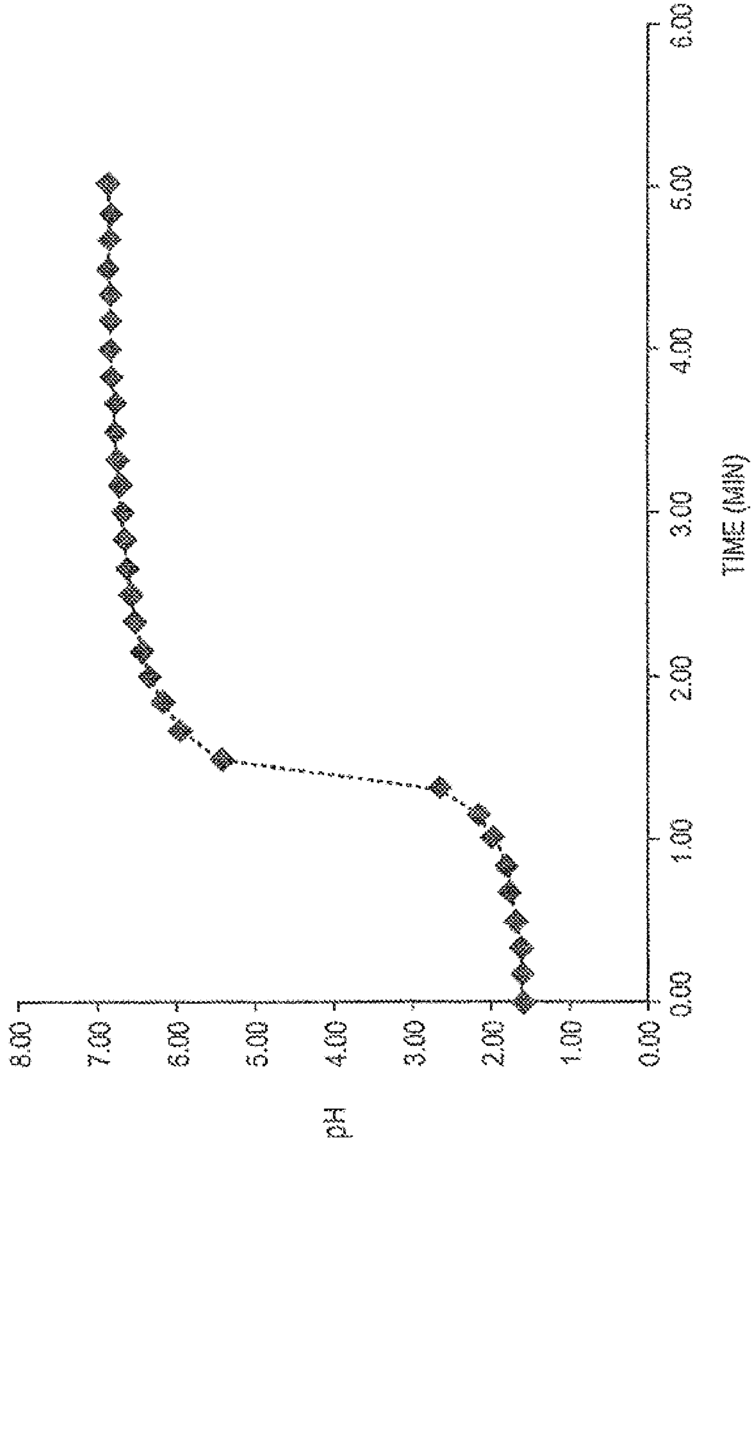
FIG. 4 shows the variation of pH of a dissolution medium when multiple tablets are added.

The prototype formulation was tableted and a dynamic test was performed where the pH modifying agents were contained in the tablets and dynamically reacted in 0.55 N HCl media (about pH 1.6). Multiple tablet doses both with and without self-regulation as well as a single dose with self-regulation were tested and compared. Dissolution media pH and drug release were monitored. As shown in FIG. 4, a rapid rise in pH in the prototype multiple tablets was observed with a rise to pH 6 occurring in less than two minutes. Thus, a rapid rise in pH can be affected by the pH modifying agents contained in the tablet.

Figure 5:
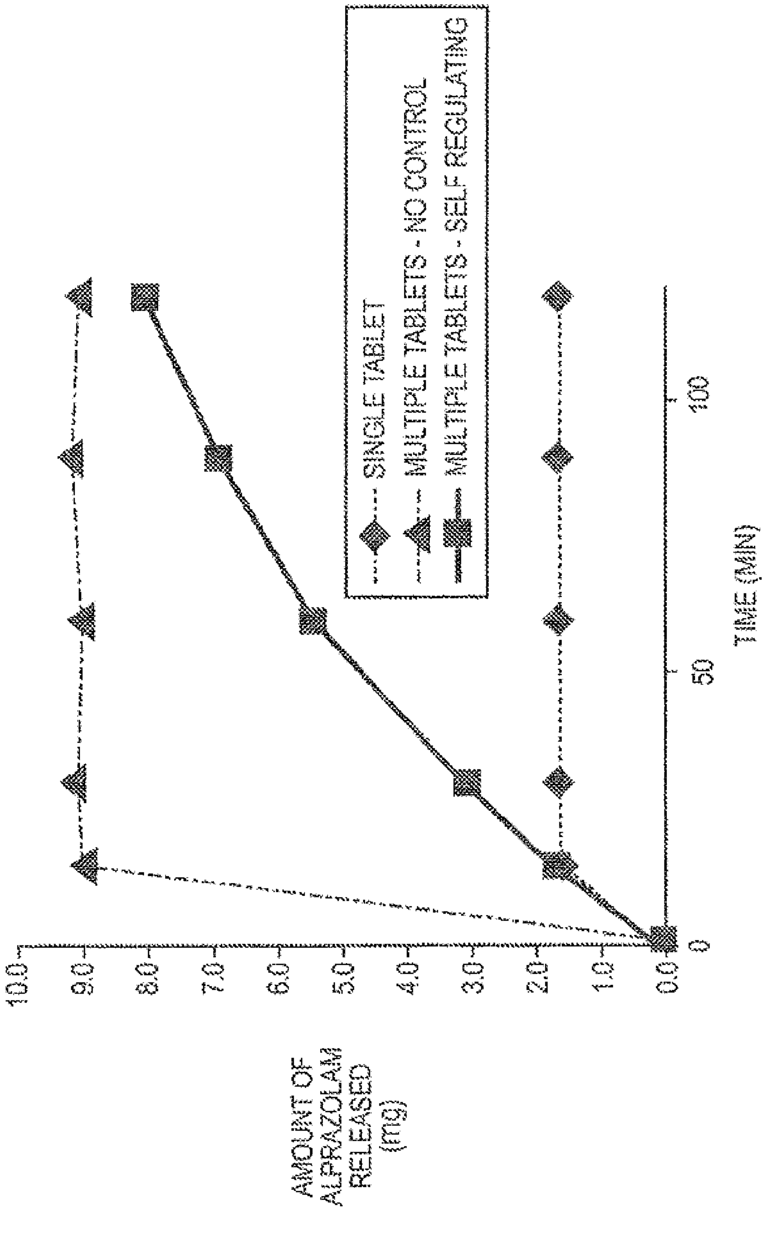
FIG. 5 shows a comparison of an in vitro active ingredient release from single and multiple table administrations.

Furthermore, as shown in FIG. 5, a single tablet releases alprazolam in 15 minutes showing that the immediate release characteristic of a single tablet is unaffected by the on-board, self-regulating system. However, multiple tablets with self-regulating show approximately a single dose released in 15 minute with a delayed release of the excess alprazolam over approximately 2 hours. By comparison, multiple tablets without self-regulating show that the entire alprazolam dose (approximately 9 mg) is released in approximately 15 minutes, whereas only 20% alprazolam is released in multiple tablets with self-regulating at the same time point. Clearly, prototype self-regulating alprazolam tablets have been shown to release a single dose of alprazolam as intended but multiple tablets show a retardation of the release of excess doses compared to excess doses without self-regulating.

It will be appreciated by persons skilled in the art that numerous variations and/or modifications may be made to the invention shown in the specific embodiments without departing from the spirit and scope of the invention as broadly described. Further, each and every reference cited above is hereby incorporated by reference as if fully set forth herein.

What is claimed is:

1. An immediate release dosage form comprising:

(a) particles comprising:

(i.) an amount of active pharmaceutical ingredient;

(ii.) a sequestering component contacting the active pharmaceutical ingredient to thereby form a particle;

(b) wherein the sequestering component comprises an acid soluble ingredient that is insoluble in water at a pH greater than 4 and is soluble in water at a pH 4 and below; wherein the dosage form demonstrates an immediate release profile of the active pharmaceutical ingredient when administered to a human in therapeutic doses and demonstrates a retarded release profile of the active ingredient when administered to a human in excess of a dosage appropriate to provide a therapeutic effect.

2. The immediate release dosage form of claim 1, wherein the particle further comprises (iii.) a buffering ingredient, wherein the buffering ingredient is in an amount sufficient to retard release of the pharmaceutically active ingredient when the composition is ingested in excess of a dosage appropriate to provide a therapeutic effect.

3. The immediate release dosage form of claim 2, wherein the buffering ingredient is in an amount sufficient to elevate a stomach pH to greater than 4 when the composition is ingested in excess of a dosage appropriate to provide a therapeutic effect.

4. The immediate release dosage form of claim 2, wherein the buffering ingredient is in an amount sufficient to suppress peak plasma concentration ($C_{max}$) of the pharmaceutically active ingredient, when the composition is ingested in excess of a dosage appropriate to provide a therapeutic effect.

5. The immediate release dosage form of claim 2, wherein the buffering ingredient is in an amount sufficient to increase a length of time ($T_{max}$) until peak plasma concentration ($C_{max}$) of the pharmaceutically active ingredient is reached, when the composition is ingested in excess of a dosage appropriate to provide a therapeutic effect.

6. The immediate release dosage form of claim 1, wherein the active pharmaceutical ingredient comprises a drug susceptible to abuse.

* * * * *